United States Patent [19]
Geary et al.

[11] Patent Number: 5,859,188
[45] Date of Patent: Jan. 12, 1999

[54] METHOD FOR DISCOVERING NOVEL ANTHELMINTIC COMPOUNDS

[75] Inventors: Timothy G. Geary, Kalamazoo; Jerry W. Bowman, Lawton; Alan R. Friedman, Portage, all of Mich.

[73] Assignee: Pharmacia & Upjohn Company, Kalamazoo, Mich.

[21] Appl. No.: 866,845

[22] Filed: May 30, 1997

Related U.S. Application Data

[60] Provisional application No. 60/019,307 Jun. 7, 1996.
[51] Int. Cl.$^6$ ........................................ A61K 38/08
[52] U.S. Cl. .................................... 530/329; 514/16
[58] Field of Search ............................. 514/16; 530/329

[56] References Cited

FOREIGN PATENT DOCUMENTS

93/21217  4/1992  WIPO ............................. C07K 7/04

OTHER PUBLICATIONS

International Journal for Parasitology, vol. 25, No. 11, 1995, T.G. Geary et al., "The Pharmacology of FMRFamide–Related Neuropeptides in Nematodes: New Opportunities for Rational Anthelminit Discovery?", pp. 1273–1280.
Keating, Parasitology III, 515, 1995.
Marks, Biochem. Biophys. Res. Commun. 217, 845, 1996.

*Primary Examiner*—Cecilia J. Tsang
*Assistant Examiner*—David Lukton
*Attorney, Agent, or Firm*—Lucy X. Yang

[57] ABSTRACT

The present invention provides a novel radioactive neuropeptide represented by the formula Lys-His-Glu-Tyr$^{-1}$-Leu-Arg-Phe-amide. The invention also provides a method for detecting anthelmintic activity of a compound using the novel neuropeptide of the present invention in a receptor binding assay. The novel radioactive neuropeptide has potent bioactivity in *Ascaris suum* neuromuscular strips, and therefore is particularly useful for high volume screening for potential anthelmintic compounds.

8 Claims, 1 Drawing Sheet

AF1 (1 nm) AND MONO-RADIOIODINATED AF2 (1 nm) INDUCED
TENSION CHANGE OVER TIME ON *A. summ* INNERVATED MUSCLE STRIPS

METHOD FOR DISCOVERING NOVEL ANTHELMINTIC COMPOUNDS

CROSS-REFERENCE TO RELATED APPLICATION

This application claims the benefit of the following provisional application: U.S. Ser. No. 60/019,307, filed Jun. 7, 1996, under 35 USC 119(e)(i).

FIELD OF THE INVENTION

The present invention relates to a method for discovering novel anthelmintic compounds. More particularly, the present invention relates to a radioligand receptor binding assay using a novel potent radioactive neuropeptide for discovering novel anthelmintic compounds.

BACKGROUND OF THE INVENTION

During the millions of years that animals and plants have competed among themselves for food and space, parasites have invaded practically every kind of living organism. The fact that many parasites cause diseases is of particular concern to the health of humans and animals throughout the world.

Discovery of drugs effective against helminth parasites has been an endeavor of rare successes. Finding molecules that safely cure infections by a diverse array of parasitic helminths presents a strong challenge, one that has so far been met only through the laborious process of screening synthetic compounds or fermentation extracts for toxicity to whole organisms. A useful broad spectrum anthelmintic class has been discovered about once per decade, but it has now been almost 20 years since the prototype of the newest class, the avermectins, was found. The dearth of useful new anthelmintic templates can be blamed on many factors, but an undeniable cause is the inefficiency of current methods for discovering parasiticides, which have not kept pace with improvements made in other therapeutic arenas. See Geary, T. G. et al., *International Journal for Parasitology*, Vol. 25, No. 11, pp.1273–1280 (1995).

FMRFamide-related peptides (FaRPs) are ubiquitous neuropeptides of invertebrates and have profound physiological effects on their neuromuscular systems. These neuropeptides are not found in vertebrates, making them attractive targets for anthelmintic discovery. A number of FMRFamide-related peptides have now been isolated from representative nematodes and other helminths, arthropods, molluscs and annelids, which offers the possibility of specific targeting of these parasites and other invertebrate parasites and insects. See Price, D. A. and Greenberg, M. J., *Biological Bulletin*, Vol. 177, pp. 190–205 (1989); Stretton, A. O. W. et al., *Parasitology*, Vol. 102, pp. S107–S116 (1991); Maule, A. G. et al., *Parasitology*, Vol. 109, pp. 351–356 (1994); Geary, T. G. et al., *International Journal for Parasitology*, Vol. 25, No. 11, pp.1273–1280 (1995); Halton, D. W., et al., *Advances in Parasitology*, Vol. 34, pp. 163–227 (1994); Walker, R. J., *Comparative Biochemistry and Physiology*, Vol. 102C, pp. 213–222 (1992); Maule, A. G. et al., *Parasitology*, Vol. 113, Supplement pp S119–S135 (1996); Maule, A. G. et al., *Parasitology Today*, Vol. 12, No. 9, pp 351–357 (1996).

The present invention provides a new method of screening molecules in order to identify compounds useful as anthelmintic drugs. The present invention provides a novel radioactive FMRFamide-related peptide as a screening tool in receptor binding assays for detecting candidate anthelmintic molecules, in which molecules are not assessed for the ability to cause effects on the whole organism, but the ability to interact with a specific molecular target. The novel radioactive FMRFamide-related peptide of the present invention has potent bioactivity in *Ascaris suum* neuromuscular strips. Therefore, used as a screening tool in a mechanism-based receptor binding assay, it can provide information on thousands of test compounds in a short period of time while utilizing limited amounts of radioligand, drug, and animal tissue.

INFORMATION DISCLOSURE

International Publication No. WO 93/21217 discloses new peptides having formula $X^1RX^2RF-NH_2$, wherein R and F are respectively arginine and phenylalanine, $X^2$ is proline or threonine and $X^1$ is a hydroxy group. The compounds are analogues of invertebrate neuropeptides.

SUMMARY OF THE INVENTION

The present invention features a novel radioactive neuropeptide represented by the formula Lys-His-Glu-Tyr$^{-I}$-Leu-Arg-Phe-amide. The invention also features a method for detecting anthelmintic activity of a compound using said novel radioactive neuropeptide of the present invention in a receptor binding assay. The novel radioactive neuropeptide has potent bioactivity in *Ascaris suum* neuromuscular strips, and therefore is particularly useful in high volume screening of potential anthelmintic compounds.

DETAILED DESCRIPTION OF THE INVENTION

Figure 1:
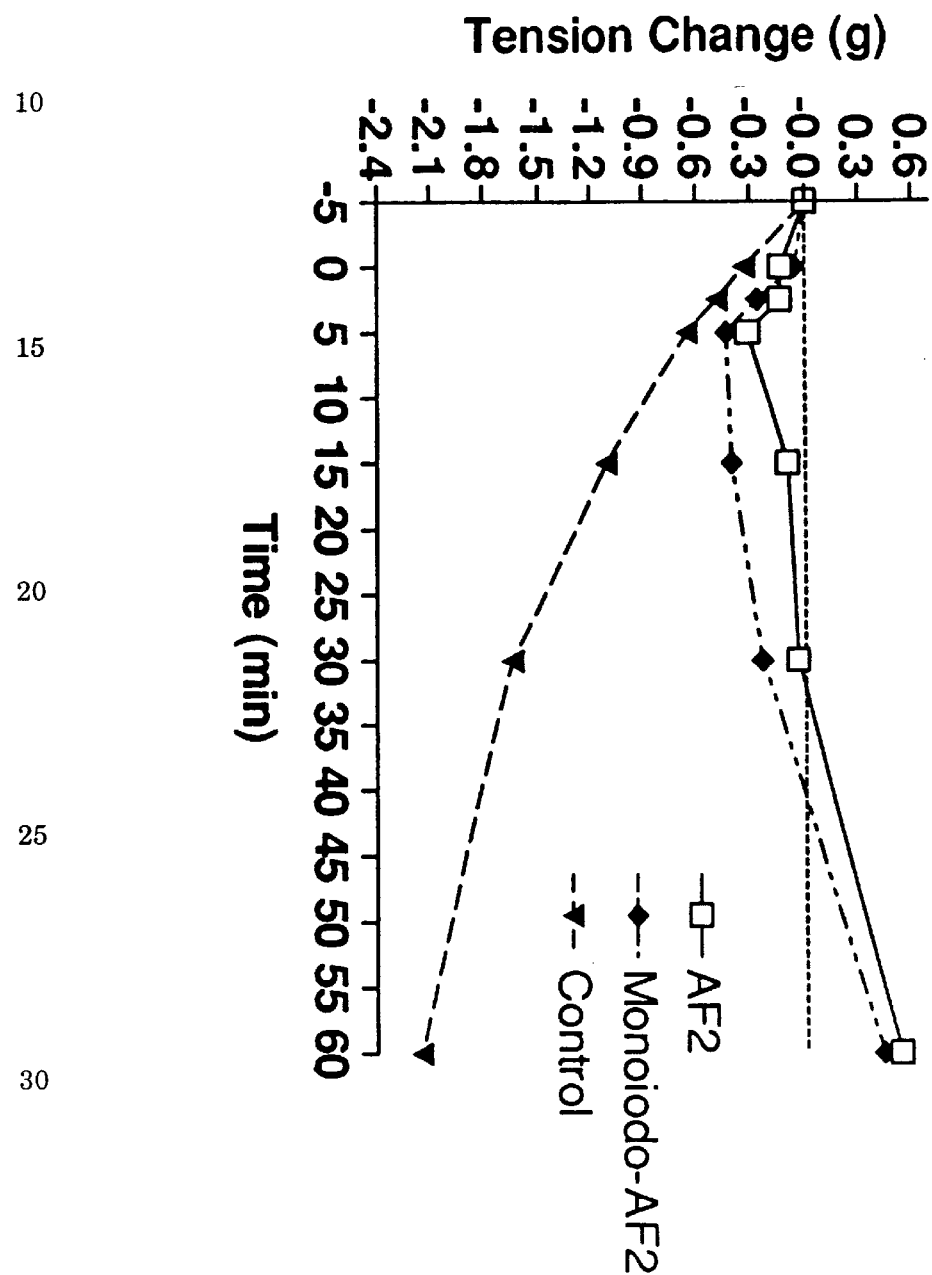

Considerable lines of evidence in the literature support the concept that compounds that act on nematode neuromusculature have anthelmintic activity. Therefore, it is expected that compounds that alter neuromuscular activity by mimicking or blocking the effects of native neuropeptides will have anthelmintic properties. Such compounds can be detected by their ability to displace a native neuropeptide from its receptor binding sites in a radioligand binding screen.

Two excitatory peptides, KNEFIRFamide (AF1) and KHEYLRFamide (AF2), are FMRFamide-related peptides originally isolated from *Ascaris suum*. These peptides are potent modulators of neuromuscular activity in the parasitic species *Ascaris suum*. AF1 and AF2 have indistinguishable physiological effects, except that AF2 is found to be approximately 1000-fold more potent than AF1. See Bowman, J. W. et al., *Peptides*, Vol 17, No. 3, pp. 381–387 (1996). Therefore, it is particularly desirable to synthesize a radioactive AF2 derivative which retains full potency and efficacy for high volume binding screening to identify compounds useful as anthelmintic agents. These qualities are important in order for a radioactive ligand to be useful in a receptor-binding screen. The literature teaches that ligands which have low affinity for a receptor, with dissociation constant greater than $2\times10^{-7}M$, are not useful for receptor binding studies, and dissociation constants between $10^{-10}$ and $10^{-8}M$ are preferred. See Williams, M., *Medicinal Research Reviews*, Vol. 11, No.2, pp. 147–184. A further desirable characteristic of ligands for a binding assay screen is that specific binding be $\geq 80\%$ to minimize random noise between samples. See Sweetnam, P. M. et al., *Journal of Natural Products*, Vol. 56, No. 4, pp. 441–455. Ligands with specific binding <60% are not recommended for binding screens.

It has been disclosed in publications that each amino acid residue in AF1 contributes to the biological activity of the parent peptide, and alterations in any part of AF1 has profound effects on the activity. See Geary, T. G. et al., *International Journal for Parasitology*, Vol. 25, No. 11, pp. 1273–1280 (1995); Bowman, J. W. et al., *Peptides*, Vol 17, No. 3, pp. 1–7 (1996). For example, the potency of AF1 is greatly reduced by alanine substitution for any residue. Elimination of functional groups or amino acids at either end of the peptide is deleterious. Peptides that contained features of both AF1 and AF2 are either equipotent with AF1 (and therefore much less potent than AF2) or considerably less potent than AF1. The results are summarized in Table 1.

TABLE 1

SUMMARY OF AF1 ANALOGUE BIOACTIVITY IN AN A. suum MUSCLE TENSION ASSAY

| Peptide | Threshold Concentration |
|---|---|
| KNEFIRFamide (AF1) | 10 nM |
| Length modifications | |
| KNEFIRF-OH (AF1 acid) | ND |
| NEFIRFamide | ND |
| FIRFamide | ND |
| Alanine substitutions | |
| ANEFIRFamide | ND |
| KAEFIRFamide | ND |
| KNAFIRFamide | 100 nM |
| KNEAIRFamide | 3.2 μM |
| KNEFARFamide | 10 μM |
| KNEFIAFamide | 10 μM |
| KNEFIRAamide | ND |
| AF1/AF2 hybrids | |
| KHEYLRFamide | 10 pM |
| KNEYIRFamide | 3.2 μM |
| KNEFLRFamide | 3.2 μM |
| KHEYIRFamide | 10 nM |

In Table 1, "Threshold Concentration" means the lowest tested concentration of peptide that detectably altered tension and/or contractile activity in at least half the strips examined; "ND" means no detectable effect at 10 μM. These results indicate that each amino acid plays a critical role in the physiology of AF1. They also suggest that modifications in AF2 would have similar undesirable effects on its bioactivity. In order to define the amino acids essential for the biological activity of AF2, we studied the ability of alanine substituted AF2 analogues to displace radioactive AF2 in a binding assay. Only one analogue retains full bioactivity, whereas alanine substitution for any other amino acid reduced potency below useful levels. The results are demonstrated in Table 2. An example of an insufficiently potent analogue is the alanine substitution for tyrosine (ala—4 AF2), a finding which demonstrates that modification of this position is deleterious for activity. This result is consistent with the alanine-for-phenylalanine substitution in the AF1 series and the poor activity of the tyrosine for phenylalanine substitution in AF1.

TABLE 2

SUBSTITUTED AF2 ANALOGUES TO DISPLACE RADIOACTIVE AF2 IN A BINDING ASSAY

| AF2 and Derivatives | $IC_{50}/nM$ |
|---|---|
| KHEYLRFamide (AF2) | 0.2 |
| KHEYL*RFamide (reduced bond) | 20 |
| KHEYLRF-OH (AF2 acid) | 900 |

TABLE 2-continued

SUBSTITUTED AF2 ANALOGUES TO DISPLACE RADIOACTIVE AF2 IN A BINDING ASSAY

| AF2 and Derivatives | $IC_{50}/nM$ |
|---|---|
| AF2-AF1 Hybrids | |
| KHEYIRFamide | 1 |
| KNEFLRFamide | 95 |
| AF2 Alanine Scan | |
| AHEYLRFamide | 500 |
| KAEYLRFamide | 270 |
| KHAYLRFamide | 0.3 |
| KHEALRFamide | 280 |
| KHEYARFamide | 600 |
| KHEYLAFamide | No Displacement |
| KHEYLRAamide | 2000 |
| Other Related Peptides | |
| KNEFIRFamide (AF1) | 1000 |
| KNEFIRF-OH (AF1 Acid) | No Displacement |
| KSAYMRFa (PF3) | No Displacement |
| KPNFIRFamide (PF4) | 10000 |
| YLRFamide | No Displacement |

However, it has been surprisingly discovered that the substitution of an iodine, both $^{127}I$ and $^{125}I$, for H on the phenyl ring of tyrosine in AF2 retains full potency and efficacy. Accordingly, the present invention provides a novel potent radioactive neuropeptide represented by the formula Lys-His-Glu-Tyr$^{-I}$-Leu-Arg-Phe-amide, which is useful in high volume binding screening to identify anthelmintic compounds. The discovery that iodo-AF2 displays useful specific binding (>80% in the current embodiment) is unanticipated based on previous studies with a radioactive derivative of another nematode FMRFamide-related peptide, PF1 (Ser-Asp-Pro-Asn-Phe-Leu-Arg-Phe-$NH_2$; SDPNFLRFamide). When PF1 is radiolabelled by exchanging a tritium atom for one of the hydrogen atoms on the leucine moiety ([$^3H$]PF1), only 40% specific binding is observed in *Ascaris suum* tissues. See Bowman, J. B. et al., *Journal of Neurophysiology*, Vol. 74, pp. 1880–1888 (1995). The fact that a radioactive analogue of a nematode neuropeptide in the same family as AF2 was shown to be not useful for receptor binding screens demonstrates that utility of radioactive FaRPs for this purpose cannot be predicted. The value of a radioactive analogue of AF2 for screening purposes is enhanced by the fact that AF2 is found broadly among the nematodes, is generally the most abundant FaRP present in these organisms, is the most potent peptide in the *Ascaris suum* muscle preparation, and also has activity in bioassays against other helminths, specifically against the parasite *Fasciola hapatica*. See Geary, T. G., *International Journal for Parasitology*, Vol. 25, No. 11, pp. 1273–1280, 1995;

DEFINITIONS

The following single letter abbreviations of the amino acids are used in this specification:

K—lysine (Lys)
H—histidine (His)
E—glutamic acid (Glu)
Y—tyrosine (Tyr)
L—leucine (Leu)

R—arginine (Arg)
F—phenylalanine (Phe)
M—methionine (Met)
N—asparagine (Asn)
I—isoleucine (Ile)

The standard 3-letter abbreviations are also used to identify the amino acid residues, and where the amino acid residue has isomeric forms, it is the L-form of the amino acid that is represented unless otherwise expressly indicated.

The term "FaRPs" refers to FMRFamide-related peptides.

The term "FMRFamide-related peptides" refers to neuropeptides with the C-terminal motif ZXRF—$NH_2$, wherein Z is Phe or Tyr; and X is Met, Leu, or Ile.

The term AF1 refers to a peptide presented by the sequence Lys-Asn-Glu-Phe-Ile-Arg-Phe-amide.

The term AF2 refers to a peptide presented by the sequence Lys-His-Glu-Tyr-Leu-Arg-Phe-amide.

The term "iodinated AF2" means mono-iodinated AF2, i.e., an AF2 peptide in which a hydrogen on the phenyl ring of tyrosine is substituted by an iodine atom.

The term "receptor preparation" means a membrane fraction obtained from muscle or nerve tissue of a nematode, e.g. *Ascaris suum*.

PREPARATION OF AF2

AF2 is synthesized by the solid phase method using Fmoc chemistry on a peptide synthesizer. Verification of authenticity and purity is obtained via amino acid analysis and mass spectrometry. The synthetic and analytical methods are described in further detail in Maule, A. G., Shaw, C., Browman, J. W. et al., *Peptides*, Vol. 16, No. 1, pp. 87–93 (1994); Fields, C. G. et al., *Peptide Research*, Vol. 4, pp. 95–101 (1991); Maule, A. G., Shaw, C., Browman, J. W. et al., *Biochemical and Biophysical Research Communications*, Vol. 200, pp. 973–980 (1994).

PREPARATION OF MONO-RADIOIODINATED AF2

The nematode neuropeptide AF2 (KHEYLRFamide) is iodinated utilizing a typical chloramine T protocol. To a 2 ml vial is added 10 µl of a 1 mM water solution of AF2, 10 µl of 0.1M, pH 7.99, sodium phosphate buffer, 0.5 mCi [$^{125}$I] sodium iodide and 5 µl of a 2 mg/ml chloramine T solution (in the phosphate buffer). The mixture is vortexed for 60 seconds and the reaction stopped by the addition of 25 µl of a 5 mg/ml solution of sodium metabisulfite in phosphate buffer. The mixture then undergoes HPLC separation by injecting it onto a Vydac C18 (0.45×15 cm) column and subjecting it to gradient separation. The gradient used is 80% A and 20% B at time zero to 45% A and 55% B at time 30 minutes (A=0.1M $NH_4$ acetate in water, B=0.1M $NH_4$ acetate in water 40%: $CH_3CN$ 60%, v:v). Flow rate is 1.0 ml/minutes. Samples are collected into 0.5 ml capture buffer (0.1M sodium phosphate buffer with 0.5% bovine serum albumin, 0.1% Triton X100 and 0.05% Tween 20) at 30 second intervals from t=15 minutes to t=30 minutes. Monoiodo AF2 typically elutes at t=22 minutes. Yield is approximately 150 uCi monoiodo AF2 in 1 ml.

POTENCY EVALUATION

AF2 and iodinated AF2 were evaluated in a bioassay using an innervated *Ascaris suum* muscle preparation and potency was estimated by measuring the physiological effects of the peptides on *A. suum* muscle tension and contractile frequency.

An adult female was bisected transversely just anterior to the oviduct. A 2 cm segment was obtained anterior from the initial cut and that section was placed immediately under 37° C. medium in a dissection chamber. Two muscle strips were then prepared from each segment. Strips were prepared by cutting the segment longitudinally along one lateral line, removing the gut and then severing the opposite lateral line. Steel wires, 4 cm long, 0.25 mm diameter, with terminal sharpened hooks, were inserted through the muscle strip approximately 3 mm and centered from each end. These hooks were used to suspend the muscle strip between an isometric force transducer and a stationary holdfast in a 37° C. water jacketed incubation chamber filled with suppressive Ascaris Ringer's Solution constantly bubbled with $N_2$. The transducer was connected to a Gould chart recorder via a Gould Universal amplifier.

The muscle tension on each preparation was "normalized" to zero five minutes before the addition of a test compound or vehicle. Compounds or vehicles were introduced from stock solutions and assayed at a final concentration of 1 nM in replicate (n=6). AF2 and mono-iodinated AF2 have been observed to produce qualitatively and quantitatively similar characteristic biphasic responses (short term inhibition followed by long term excitation) in this bioassay. Inhibition is manifested as a drop in baseline tension (compared to control), while excitation is defined as a marked rise in baseline tension, often superimposed with transient muscle contractions (spiking). In order to estimate the net change in muscle tension of these preparations, the midpoint of the spike was estimated visually. Muscle tension data were analyzed by analysis of variance.

Table 3 presents the mean muscle tension date (5, 15, 30 and 60 minutes after peptide addition). At 1 nM, AF2 and iodinated AF2 have similar effects on muscle tension in the Ascaris preparations. AF2 and iodinated AF2 were not statistically different at any of the time periods analyzed.

FIG. 1 illustrates tension changes induced by AF2 (1 nM) and iodinated AF2 (1 nM) over time on *A. suum* innervated muscle strips. Spike amplitude data indicated a significant increase in this parameter following treatment with either AF2 or iodinated AF2.

TABLE 3

EFFECT OF PEPTIDES ON MUSCLE TENSION
OF INNERVATED A. summ MUSCLE PREPARATIONS

| Time (min.) | 5 | 15 | 30 | 60 |
|---|---|---|---|---|
| Treatment/ | Tension | Tension | Tension | Tension |
| Preparation | (mg) | (mg) | (mg) | (mg) |
| Control | −650 | −1108 | −1642 | −2142 |
| Iodo AF2 | −430 | −403 | −237 | −437 |
| AF2 | −313 | −100 | 43 | 535 |

BINDING ASSAY

High volume radioligand binding screening to detect drug activity is relatively recent technique, and has been reported in a number of journals, including Burch, R. M., *Journal of Receptor Research*, Vol. 11, pp. 101–113 (1991); Sweetnam, P. M. et al., *Journal of Natural Products,* Vol. 56, No. 4 pp. 441–455 (1993); Williams, M., *Medicinal Research Reviews,* Vol. 11, No. 2, pp. 147–184 (1991); Burch, R. M., *Pharmaceutical Research,* Vol. 8, No. 2 pp. 141–147 (1991). The disclosure of which is incorporated herein by reference. Although radioligand binding techniques have been widely used, there is no report with regard to screening for compounds that specifically interact with a helminth neuropeptide receptor. In order to more fully illustrate the nature of the invention and the manner of practicing the same, the following binding assay is presented, but it should not be taken as a limitation.

A. Nematode Procurement

Adult female *Ascaris suum,* swine intestinal parasites, are collected in an abattoir after their removal from the intestine using pressurized water. Healthy specimens over 25 cm are selected, rinsed and placed in Ascaris Ringer's Solution (ARS: 4 mM NaCl, 5.9 mM $CaCl_2$, 4.9 mM $MgCl_2$, 5 mM Tris ($C_4H_{11}NO_3$), 125 mM $NaC_2H_3O_2$, 24.5 mM KCl, pH=7.4) at 37° C. Specimens are placed in a thermos filled with 37C Ascaris Ringer's solution and immediately air shipped to our laboratory. Upon arrival they are placed in fresh ARS (changed daily) and maintained at 37° C. for up to 3–4 days prior to use.

B. Receptor Preparation

*Ascaris suum* body wall tissue (muscle) is dissected out by pinning each specimen in a dissection tray, opening the worm along its entire length at the lateral line with a scalpel, removing the intestine and ovaries and then scraping the muscle from the cuticle. One worm yields approximately 1.0 g tissue. Tissue collected is flash frozen in liquid nitrogen and stored at −80° C. until needed.

Membrane suspension for the binding assay is prepared as follows. Collected frozen muscle is thawed in ice-cold buffer (10 mM POPSO, 2 mM EDTA, 100 uM PMSF, pH 7.4) at 7 g tissue/200 ml buffer. Tissue is broken up with a polytron for 60 seconds at setting 5 (50%). This suspension is then centrifuged at 3000 rpm for 5 minutes and the pellet discarded. The supernatant is centrifuged at 28000 g for 20 minutes. The resultant pellet is washed and centrifuged 3 times under identical conditions with the exception that a buffer containing 50 mM POPSO instead of 10 mM is used. Pellets are resuspended in the 50 mM POPSO buffer (~8 mg/ml) and stored at −80° C.

C. Binding Assay

Each replicate is one well of a standard 96-well plate and has a volume of 200 μl containing 15 ug protein (preparation described above). Each test group contains two replicates. For each test compound, one group is run with $[^{125}I]$AF2 (0.2 nM) only (for total binding) and one with 1 μM (or as designated) concentration of the test compound and $[^{125}I]$AF2 (for non-specific binding). The order of adding reagents to each replicate is: assay buffer (150 mM NaCl, 4 mM $CaCl_2$, 2 mM $MgCl_2$, 10 mM KCl, 4 mM $NaHCO_3$, 5 mM HEPES, 1 mM PMSF, 1 mM β-mercaptoethanol, 1% BSA), test compound (made up in assay buffer), $[^{125}I]$AF2 (in assay buffer) and membrane suspension (in assay buffer). The addition of the membrane suspension initiates the binding reaction which is run for 30 minutes on ice (4° C). Following the 30 minute incubation, each plate is centrifuged (4° C., 1500 g, 15 minutes) and the supernatant removed by suction. The pellet is washed with 200 μl assay buffer and the centrifugation/suction repeated. 50 μl of scintillant is added to each well and the plate is sealed. The plate is shaken on a rotary shaker for 2 hours and then counted on a Top Count® scintillation counter. The mean non-specific binding is subtracted from the mean total binding to yield specific binding for both the standard (AF2) and the unknowns.

---

What is claimed is:

1. A peptide of the formula Lys-His-Glu-Tyr$^{-I}$-Leu-Arg-Phe-amide.

2. A peptide of claim 1 which is

H—Lys—His—Glu—NH—CH(CH$_2$-C$_6$H$_3$(I)(OH))—CO—Leu—Arg—Phe—NH$_2$,

3. A peptide of claim 1 or 2 wherein the substituent iodine is a radioactive iodine.

4. A peptide of claim 3 wherein the radioactive iodine is $^{125}$I.

5. A method of detecting anthelmintic activity of a compound comprising using the peptide of claim 3 in a receptor binding assay.

6. The method of claim 5 wherein said receptor is the AF2 receptor.

7. The method of claim 5 wherein said binding assay comprising the steps of:

(a) mixing said compound and the peptide of claim 3 with AF2 receptor preparation; and (b) assaying the affinity of said compound for the AF2 receptor.

8. The method of claim 5 or 7 wherein said compound is a small non-peptide ligand.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

Lys  His  Glu  Tyr  Leu  Arg  Phe
    1                           5